(12) United States Patent
Gartside et al.

(10) Patent No.: US 7,576,251 B2
(45) Date of Patent: Aug. 18, 2009

(54) PROCESS FOR THE DOUBLE BOND HYDROISOMERIZATION OF BUTENES

(75) Inventors: Robert J. Gartside, Summit, NJ (US); Thomas P. Skourlis, Basking Ridge, NJ (US); Hassan Kaleem, Franklin Park, NJ (US)

(73) Assignee: ABB Lummus Global Inc., Bloomfield, NJ (US)

( * ) Notice: Subject to any disclaimer, the term of this patent is extended or adjusted under 35 U.S.C. 154(b) by 806 days.

(21) Appl. No.: 11/107,649

(22) Filed: Apr. 15, 2005

(65) Prior Publication Data

US 2006/0235253 A1    Oct. 19, 2006

(51) Int. Cl.
*C07C 5/25* (2006.01)
*C07C 5/27* (2006.01)

(52) U.S. Cl. .................. 585/670; 585/664; 585/646; 585/647; 585/324

(58) Field of Classification Search .............. 585/664, 585/670, 646, 647, 324
See application file for complete search history.

(56) References Cited

U.S. PATENT DOCUMENTS

| | | | |
|---|---|---|---|
| 3,531,545 A | 9/1970 | Garner et al. | 260/683.2 |
| 3,872,178 A * | 3/1975 | Tabler | 585/378 |
| 4,417,089 A | 11/1983 | Drake | 585/670 |
| 4,911,822 A | 3/1990 | Franck et al. | 208/66 |
| 5,087,780 A | 2/1992 | Arganbright | 585/259 |
| 5,595,634 A * | 1/1997 | Hearn et al. | 203/29 |
| 5,609,654 A | 3/1997 | Le et al. | 44/449 |
| 5,969,203 A | 10/1999 | Dorbon et al. | 585/324 |
| 6,072,091 A | 6/2000 | Cosyns et al. | 585/259 |
| 6,075,173 A | 6/2000 | Chodorge et al. | 585/324 |
| 6,242,661 B1 | 6/2001 | Podrebarac et al. | 585/664 |
| 6,420,619 B1 | 7/2002 | Gartside et al. | 585/324 |
| 6,583,329 B1 | 6/2003 | Podrebarac | 585/646 |
| 6,686,510 B2 | 2/2004 | Commereuc et al. | 585/324 |
| 6,743,958 B2 * | 6/2004 | Commereuc et al. | 585/324 |
| 6,777,582 B2 | 8/2004 | Gartside et al. | 585/324 |
| 6,872,862 B2 * | 3/2005 | Bridges et al. | 585/324 |

FOREIGN PATENT DOCUMENTS

WO      WO 93/21137      10/1993

OTHER PUBLICATIONS

International Search Report and Written Opinion of the International Searching Authority for PCT/US2006/014123.

* cited by examiner

*Primary Examiner*—In Suk Bullock
(74) *Attorney, Agent, or Firm*—Alix, Yale & Ristas, LLP

(57) ABSTRACT

A process is disclosed for the preferential conversion to 2-butene of a stream containing C4 compounds including 1-butene and 2-butene. The process involves mixing the C4 stream with a first hydrogen stream to form a feed stream, hydroisomerizing the feed stream in the presence of a first hydroisomerization catalyst in order to convert at least a portion of the 1-butene to 2-butene, thereby producing a hydroisomerization effluent, passing the hydroisomerization effluent through a fractionation column to form a top stream comprising isobutane and isobutylene and a bottoms stream comprising 2-butene, withdrawing a recycle stream from said fractionation column at a location above the feed point at which the weight ratio of 1-butene to 2-butene is high, and combining the recycle stream with at least one of the C4 stream and the feed stream upstream from the hydroisomerization catalyst. A corresponding apparatus also is disclosed.

21 Claims, 7 Drawing Sheets

PROCESS FOR THE DOUBLE BOND HYDROISOMERIZATION OF BUTENES

FIELD OF THE INVENTION

The present invention is directed to double bond hydroisomerization of C4 olefins.

BACKGROUND OF THE INVENTION

In many processes it is desirable to have isomerization of double bonds within a given molecule. Double bond isomerization is the movement of the position of the double bond within a molecule without changing the structure of the molecule. This is different from skeletal isomerization where the structure changes (most typically representing the interchange between the iso form and the normal form). Skeletal isomerization proceeds by a completely different mechanism that double bond isomerization. Skeletal isomerization typically occurs using a promoted acidic catalyst.

There are two basic types of double bond isomerization, namely hydroisomerization and non-hydroisomerization. The former uses small quantities of hydrogen over noble metal catalysts (such as Pt or Pd) and occurs at moderate temperatures while the latter is hydrogen free and typically employs basic metal oxide catalysts at higher temperatures.

Double bond hydroisomerization at moderate temperatures is mostly used to maximize the interior olefin (2-butene for example as opposed to 1-butene) since the thermodynamic equilibrium favors the interior olefin at lower temperatures. This technology is used when there is a reaction that favors the interior olefin over the alpha olefin. Ethylenolysis of 2-butene to make propylene is such a reaction. The ethylenolysis (metathesis) reaction is 2-butene+ethylene→2 propylenes. Ethylene and 1-butene do not react. If in a mixture of C4 normal olefins, 2-butene can be maximized, then the reaction to propylene will be maximized.

It is well known that double bond hydroisomerization reactions occur simultaneously with hydrogenation reactions. In many commercial applications, a feedstock with highly unsaturated molecules (acetylenics and/or dienes) is processed over a fixed bed of supported noble metal catalyst in the presence of hydrogen. For example, the reaction of butadiene over noble metal catalysts can be summarized in the reaction sequence shown below:

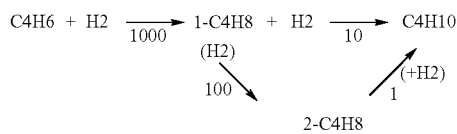

The primary hydrogenation reaction of butadiene plus hydrogen forms 1-butene. It proceeds rapidly over the catalysts (relative rate equivalent to 1000). In the presence of hydrogen, two reactions occur with 1-butene. One is the hydroisomerization to 2-butene (relative rate of 100). This reaction requires the presence of hydrogen to proceed but does not consume hydrogen. The other reaction is hydrogenation to normal butane (relative rate of 10). The final reaction is the hydrogenation of 2-butene directly to normal butane. This is the slowest reaction (relative rate of 1) and essentially can be neglected. Under normal conditions over noble metal catalysts, it is expected that the selectivity of 1-butene conversion will be 90% to 2-butene and 10% to n-butane. The latter represents a loss of olefins and is undesirable.

Hydroisomerization and hydrogenation reactions are known to be carried out in fixed bed reactors. U.S. Pat. No. 3,531,545 describes a process and method for double bond isomerization consisting of mixing a hydrocarbon stream containing 1-olefins and at least one sulfur-containing compound with hydrogen, heating the mixed hydrocarbon/hydrogen stream to reaction temperatures, contacting the stream with a noble metal catalyst, and then recovering the 2-olefins as a product. The process described in this patent utilizes sulfur as an additive to reduce the hydrogenation tendency of the catalyst and thus increase hydroisomerization. Sulfur is shown to be either present in the feed, added to the feed, or added to the hydrogen stream.

It is known to employ a hydrocarbon fractionation tower in combination with a fixed bed hydrogenation reactor. In U.S. Pat. No. 6,072,091, a distillation column is used in combination with at least one hydrogenation reaction zone. The hydrogenation reaction zone is associated with the rectification section of the distillation column. More specifically, hydrocarbons are removed from the rectification section of the column to hydrogenate at least a portion of the acetylenic and diolefinic hydrocarbons contained therein. The effluent from the reaction zone is then re-introduced into the rectification section of the distillation column.

It is known to carry out a hydroisomerization reaction within a catalytic distillation tower. In U.S. Pat. No. 5,087,780 (Arganbright), a process for the isomerization of butenes in a mixed C4 hydrocarbon stream is described. A stream containing 1-butene, 2-butene, and small amounts of butadiene is fed to a catalytic distillation tower containing a Pd catalyst. A small amount of hydrogen is also fed to the tower. The 1-butene, being the among the most volatile of the C4s, moves overhead while the 2-butene, being less volatile, tends to go toward the bottom of the tower. Catalyst is located in the zone with higher concentrations of 2-butene, and hydroisomerization of 2-butene to 1-butene occurs. Residual 2-butene in the bottom may be recycled to the tower. If isobutylene is part of the feed mixture, it will also go overhead with the 1-butene.

In U.S. Pat. No. 6,242,661 a process for the separation of isobutylene from normal butenes is disclosed. This process also employs a catalytic distillation process incorporating the hydroisomerization reaction. A mixture of normal and isobutylenes is fed to a tower along with a small amount of hydrogen. The tower contains a Pd catalyst located within distillation structures within the tower. In this process, the catalyst is located in the upper section of the tower in a multiplicity of catalyst beds. As the fractionation occurs, the isobutylene moves overhead. 1-Butene (also a volatile component) tends to move with isobutylene. Since the system does not employ a skeletal isomerization catalyst, the isobutylene moves through the tower unaffected. However, hydroisomerization occurs in the regions of high 1-butene and the 1-butene is converted to 2-butene. This 2-butene is less volatile and moves to the bottom of the tower. In this fashion, relatively pure isobutylene is obtained overhead since the 1-butene is reacted and moves to the bottom as 2-butene.

The above processes all produce a stream that is concentrated in 2-butene. In the ethylenolysis (metathesis) reaction of 2-butene to form propylene, it is known that isobutylene is not a desired feed component. Isobutylene and ethylene will not react. Isobutylene and 2-butene will react to form propylene and 2-methyl-2-butene. This reaction has a negative effect on the propylene selectivity of the ethylenolysis reaction and is not desirable. Thus in most cases, it is preferable to remove isobutylene from a 2-butene stream prior to reaction with ethylene.

It is known to use a catalytic distillation-deisobutyleneizer (CD-DeIB) to prepare a 2-butene stream for a metathesis (ethylenolysis) reactor. Similarly to U.S. Pat. No. 6,242,661 referenced above, a CD-DeIB will remove isobutylene overhead while maximizing the flow of 2-butene out the bottoms as the 1-butene is hydroisomerized to form 2-butene. The tower typically contains alternating catalyst and fractionation structures above the feed point, and fractionation structures below the feed point. Usually there are about four catalyst sections in the tower. Hydrogen is added below the feed point in order that it is sufficiently dispersed by the time it reaches the feed point.

The CD-DeIB in this service accomplishes two functions. It hydroisomerizes the 1-butene to 2-butene to improve recovery of 2-butene and maximize the production of propylene, and also hydrogenates the small remaining amounts of butadiene after the selective hydrogenation to reduce the content of butadiene, which is a poison for the metathesis catalyst. In a CD-DeIB tower, the isobutane and isobutylene are the most volatile components and tend to go overhead in the tower. The 2-butene and the n-butane are the least volatile and tend to go to the bottom. The 1-butene and butadiene have intermediate volatility and will go up or down depending upon the operation of the tower. If the tower is designed so that the 1-butene goes up, it contacts a catalyst section and is hydroisomerized to 2-butene to the limit of the 1-butene/2-butene equilibrium in the tower. The 2-butene formed from hydroisomerization of the 1-butene tends to move downward and the remaining 1-butene continues to move upward. The fractionation sections of the tower separate the 2-butene from the 1-butene.

The butadiene which enters the CD-DeIB is slightly less volatile than the 1-butene. Some of the butadiene moves upward where it is hydrogenated over the catalyst. The primary product of the hydrogenation is 1-butene. However, a portion of the butadiene that moves upward is "fully" hydrogenated to n-butane. This constitutes a loss of n-butenes and thus a loss of feed for a metathesis unit. Some of the butadiene moves downward with the primarily 2-butene product. This butadiene is unreacted since it does not come into contact with catalyst. Butadiene can be present in no more than very low levels in the bottoms if the 2-butene is to be fed to a metathesis unit.

U.S. Pat. No. 6,420,619 is directed to a process in which both a "back end" catalytic distillation-hydrogenation unit and a catalytic distillation deisobutylenizer tower are employed. This concept replaces the fixed bed selective hydrogenation units normally associated with ethylene plant fractionation systems. There are typically separate fixed bed units for the C3, C4 and C5 fractions to remove the acetylenics and diolefins to low levels prior to further processing. The system of U.S. Pat. No. 6,420,619 uses a C3 to C6 hydrocarbon feedstock from a steam cracker or FCC unit. In the "back end" CDHydro section, catalytic distillation towers are used to hydrogenate acetylenics and diolefins in the stream including butadiene, methyl acetylene and propadiene and produce a propylene product stream. The bottoms of the tower produces a $C_4+$ stream which is then sent to a fractionation system which includes a debutanizer. The $C_4$ overhead stream from the debutanizer is routed to a CD-DeIB where hydroisomerization occurs. In addition to the $C_4$ feed to the debutanizer, there is a $C_5+$ recycle from the downstream fractionation system following the metathesis unit.

Three advantages of the system disclosed in U.S. Pat. No. 6,420,619 are:

1. recycle of the $C_5+$ stream from the metathesis unit allows for a higher recycle conversion of the butenes since the conventional system uses a C4 side draw from the depropylenizer which is intended to recycle unconverted 2-butene back to the metathesis reactor,
2. the removal of heavies prevents buildup in the recycle stream, and
3. a catalyst can be used in the debutanizer that also can be used to selectively remove any traces of butadiene.

One disadvantage of a conventional CD-DeIB system is that large quantities of catalyst must be used. Another disadvantage, as indicated above, is that in order to saturate the butadiene, the fractionation tower must be designed to push the butadiene up over the catalyst. This results in a large, costly tower with very high reflux. A third disadvantage is that when the tower bottoms is to be used as a feed stream for a metathesis unit, the quantity of isobutylene in the bottoms is required to be low, thereby resulting in very high utility costs for reboiling and condensing.

An alternative to a CD-DeIB for obtaining a 2-butene feed steam is a system which employs a fixed bed hydroisomerization unit downstream from a selective hydrogenation unit. The selective hydrogenation unit first removes butadiene to low levels. Then the effluent C4 feed stream is fed to a second fixed bed reactor and hydrogen is introduced. In the fixed bed unit the 1-butene in the stream hydroisomerizes to 2-butene and the small amount of butadiene that remains reacts. The effluent then goes to a conventional fractionating tower where the isobutylene and isobutane are separated overhead and the 2-butene goes out the bottom where it enters a disengaging drum in which any excess hydrogen is vented. The remainder of the bottoms is used as feed for the metathesis unit. This process requires less catalyst than the CD-DeIB unit because of higher driving forces for the fixed bed. The fractionating tower can be designed to allow more isobutylene to pass into the bottoms effluent, thus saving on utilities and capital since a smaller tower can be used. The disadvantage of the fixed bed system is that the quantity of n-butenes recovered is slightly lower than when a CD-DeIB is used.

U.S. Pat. No. 6,686,510 is directed to the production of high-purity isobutylene and propylene from hydrocarbon fractions having four carbon atoms. The process disclosed in this document comprises three successive stages, namely 1) the selective hydrogenation of butadiene with isomerization of 1-butene into 2-butene up to thermodynamic equilibrium; 2) the separation by distillation into a top fraction containing isobutylene and a bottom fraction containing 2-butene and butane, and 3) the metathesis of the 2-butene fraction with ethylene to produce propylene.

Thus, various systems are known for preparing 2-butene streams for use as feed streams for a metathesis unit. It would be useful to develop a method and apparatus for the selective hydroisomerization of 1-butene to 2-butene which has improved efficiency over prior known systems.

SUMMARY OF THE INVENTION

A double bond hydroisomerization process for increasing the selectivity of 2-butene over 1-butene is provided. The process increases the yield of 2-butenes from a given C4 feed stream and produces a 2-butene stream containing a lower concentration of butadiene, thereby resulting in less fouling of the downstream catalyst during a subsequent process such as metathesis.

The invention in a preferred form is a process for the preferential conversion to 2-butene of a C4 stream containing 1-butene and 2-butene, comprising mixing the C4 stream with a first hydrogen stream to form a feed stream, hydroisomerizing the feed stream in the presence of a first hydroisomerization catalyst in order to convert at least a portion of the 1-butene to 2-butene, thereby producing a hydroisomerization effluent, passing the hydroisomerization effluent through a fractionation column to form a top stream comprising isobutane and isobutylene and a bottoms stream comprising 2-butene, withdrawing a recycle stream from the fractionation column at a location above the feed point at which the weight ratio of 1-butene to 2-butene is high, and combining the recycle stream with at least one of the C4 stream and the feed stream upstream from the hydroisomerization catalyst. Withdrawal preferably takes place at an elevation in the column at which the 1-butene concentration would be at a maximum if the step of withdrawing the recycle stream were eliminated.

In one preferred embodiment, the feed stream further comprises butadiene, and the method further comprises hydrogenating the feed stream upstream from the hydroisomerization reactor to reduce the butadiene content of the C4 stream to no more than about 1 wt %. The recycle stream preferably is mixed with the feed stream after the feed stream has been hydrogenated.

In another form, the process further comprises mixing the bottoms stream with a suitable metathesis reactant to form a metathesis feed stream, and feeding the metathesis feed stream to a metathesis reactor and reacting the 2-butene with the metathesis reactant to form a metathesis product. Usually, the metathesis reactant comprises ethylene and the metathesis product comprises propylene.

Sometimes, the feed stream further includes C5 and/or heavier components, and the method further comprises removing the C5 and/or heavier components from the hydroisomerization effluent prior to fractionation. In some cases, the bottoms stream or the metathesis feed stream is purified before the metathesis feed stream is sent to the metathesis reactor.

In one embodiment, a second hydrogen stream is fed to the hydroisomerization reactor at a location downstream from the feed point of the first hydrogen stream. In some cases, a third hydrogen stream is fed to the fractionation column at a location downstream from the feed point of the second hydrogen stream. One, two or all three of the hydrogen streams optionally may further comprise carbon monoxide.

In another form, the method further comprises the step of separating the metathesis product from heavier components to form a heavy component stream and combining the heavy component stream with the hydroisomerization effluent.

Usually, the top stream and the bottoms stream each contain small quantities of 1-butene. In some cases, the flow rate of 1-butene in the top stream is greater than the flow rate of 1-butene in the bottoms stream. In other cases, the flow rate of 1-butene in the bottoms stream is greater than the flow rate of 1-butene in the top stream. The hydroisomerization catalyst in the fixed bed hydroisomerization reactor frequently comprises a group VIII metal on a support. An additive of gold, silver, and/or alkali metals also can be included.

Another embodiment is an apparatus for the preferential conversion to 2-butene of a feed stream containing hydrogen and C4 compounds, including 1-butene and 2-butene. The apparatus comprises a hydroisomerization reactor configured to contain a hydroisomerization catalyst for converting at least a portion of the 1-butene in the feed stream to 2-butene, a fractionation column for separating the hydroisomerized feed stream into a top stream comprising isobutane and isobutylene, and a bottoms stream comprising 2-butene, a side draw near the top of the fractionation column for removing a recycle stream, and a recycle inlet for combining the recycle stream with the feed stream upstream from the hydroisomerization catalyst.

The invention accordingly comprises the several steps and the relation of one or more of such steps with respect to each of the others and the apparatus possessing the features, properties and relation of elements exemplified in the following detailed disclosure.

DETAILED DESCRIPTION OF THE INVENTION

The invention provides an apparatus and method for obtaining improved yields of 2-butene from a C4 stream as compared to prior known techniques. According to the invention, a fixed bed hydroisomerization reactor is used in conjunction with a deisobutylenizer tower. A side draw is removed from the tower at a location at which the driving force for the hydroisomerization reaction to 2-butene is high and this side draw is recycled to the fixed bed hydroisomerization reactor.

Figure 1:
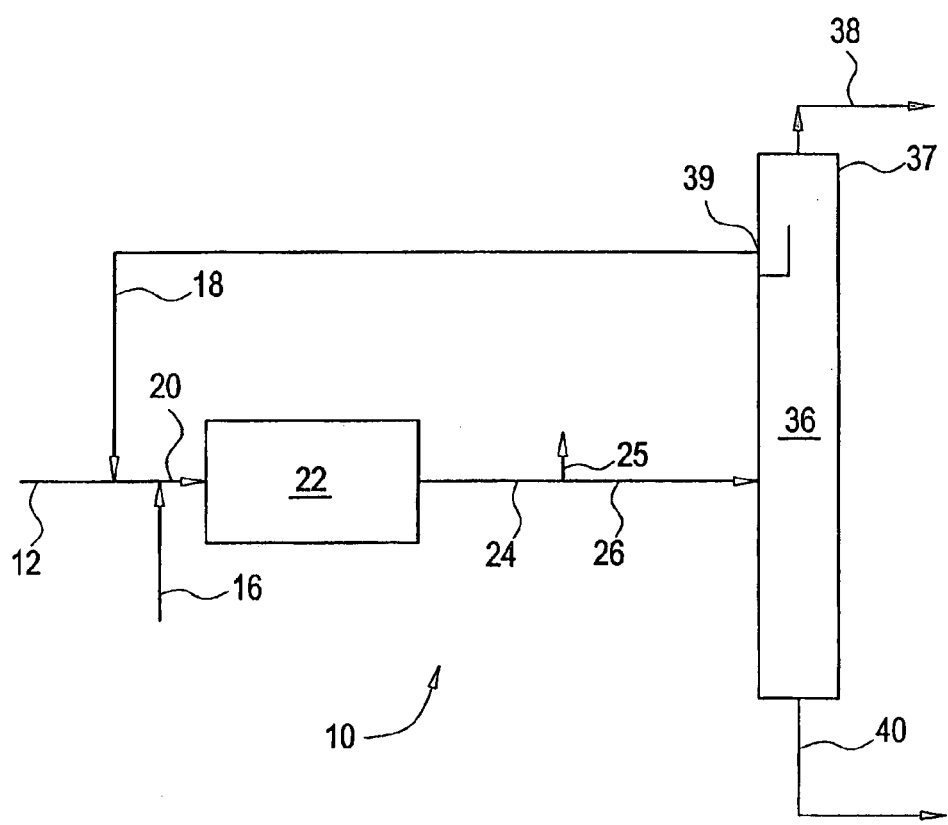
FIG. 1 is a schematic drawing of a first embodiment in which a 2-butene stream is produced.

Referring to the drawings and first to FIG. 1, an apparatus and process are shown for producing a 2-butene stream from a C4 stream. The C4 stream contains 1-butene and 2-butene, and typically also contains butadiene and butane. This stream often also contains some C5 and higher molecular weight materials. The overall process is designated as 10. A C4 stream, which is designated as 12, is combined with a recycle stream 18 to form stream 20, which is fed to a fixed bed hydroisomerization reactor 22. A typical C4 feed stream to the hydroisomerization reactor 22 contains 2-50 parts by weight 1-butene, 2-50 parts by weight 2-butene, 2-50 parts by weight isobutylene, 2-50 parts by weight isobutane, 2-50 parts by weight n-butane and 0-1 part by weight butadiene, the total parts by weight being 100. In many cases, butadiene is no more than 1500 ppmw. Hydrogen in stream 16 is fed directly to the hydroisomerization reactor 22 or is combined with streams 12 and 18 to form stream 20. In the hydroisomerization reactor 22, 1-butene is hydroisomerized into 2-butene. Typical reactor pressures are 2-30 barg, and usually 5-18 barg. Typical reactor inlet temperatures are 80-250 Deg. F.

and usually 120-180 Deg. F. Hydrogen and other non-condensibles are vented from the reactor effluent stream 24 in stream 25. Any suitable hydroisomerization catalyst can be used. Examples of such catalysts are noble metals (ca. Pd) supported on alumina. Additives to the metals including Ag, Au, etc can be used to modify the reaction characteristics. The remainder of the reactor effluent, in stream 26, is fed to a deisobutylenizer tower 36. Typical tower temperatures are 80-220 Deg. F. and usually 100-160 Deg. F. Typical reactor pressures are 2-12 barg and usually 3-8 barg. The top stream 38 from the deisobutylenizer tower 36 contains isobutylene and isobutane. Small quantities of 1-butene and 2-butene typically are included in the top stream 38. The bottoms stream 40 contains most of the 2-butene.

In accordance with the invention, a portion of the liquid is removed from the upper end 37 of the column in an upper side draw 39. The side draw 39 preferably constitutes the recycle stream 18, which is combined with feed stream 12 as is indicated above, thereby providing for additional conversion of the 1-butene present in stream 18 in the hydroisomerization reactor 22. As a result of the side draw 39, the embodiment of FIG. 1 uses significantly less catalyst than a conventional CD-DeIB process. Furthermore, the embodiment of FIG. 1 converts more of the 1-butene originating in the C4 feed stream 12 into 2-butene as compared to a conventional system employing a fixed bed and fractionating tower in which no a side draw is used.

The side draw 39 preferably is positioned at the elevation in deisobutylenizer tower 36 at which the 1-butene concentration would be the highest if no side draw were included. Typically, this is near the top of the column. To determine the appropriate elevation for the side draw in a particular system, the point of maximum driving force for the hydroisomerization reaction is determined at the conditions under which the column is set to operate. The reaction between 1-butene and 2-butene can be represented by equation (1) where B1 is 1-butene, B2 is 2 butene, $k_{b1}$ is the reaction k for B1 to B2 and $k_{b2}$ is the reaction k for B2 to B1.

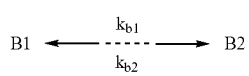
(1)

The rate of reaction is the reaction k times the concentration of the reactant. The ratio of the reaction k's, the equilibrium coefficient $K_{eq}$, is equal to the ratio of $k_{b1}$ to $k_{b2}$. The rate of the disappearance of B1 via hydroisomerization from B1 to B2 is:

Rate=$-k_{b1}[B1]+k_{b2}[B2]$

Where [B1] and [B2] are the mole percentage of 1 and 2 butene respectively. The driving force for reaction of 1 butene can be defined by dividing both sides by $-k_{b1}$ results in the following:

Driving force=$[B1]-[B2]/K_{eq}$.

This driving force factor can be plotted as a function of position in the tower for a particular system and is the preferred technique for locating the optimal point for the side draw location.

Figure 2:
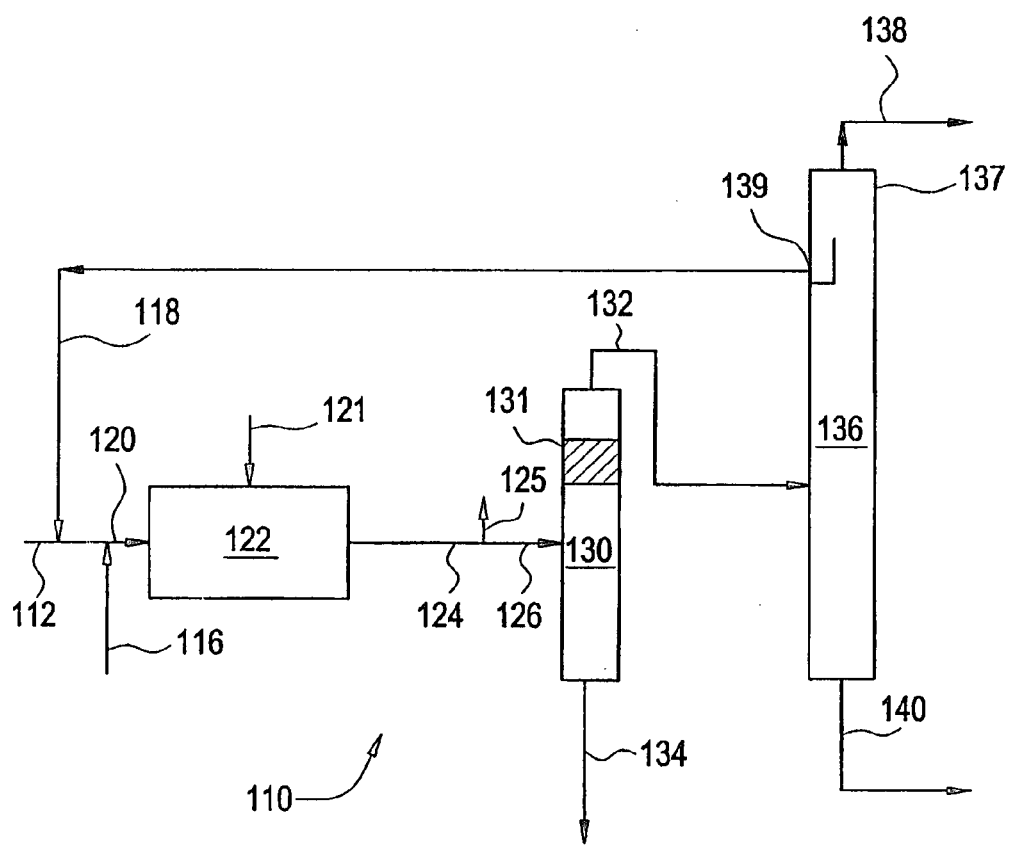
FIG. 2 is a schematic drawing of a second embodiment in which a 2-butene stream is produced, with C5+ compounds being removed prior to fractionation of the C4 compounds.

Referring next to FIG. 2, another embodiment is shown for producing a 2-butene stream from a C4 feed stream in which a side draw is removed from a deisobutylenizer tower. In this embodiment, any C5+ compounds in the feed or heavier sulfur compounds in the feed are removed upstream from the deisobutylenizer tower. Furthermore, the production of butanes during the hydroisomerization reaction is minimized by the use of multiple hydrogen feed streams and/or the inclusion of small quantities of carbon monoxide in one or more of the hydrogen streams. The inventors have surprisingly found that CO acts as an inhibitor for the hydrogenation reactions of butenes to butanes while allowing the double bond hydroisomerization reactions to continue. By feeding the hydrogen or the hydrogen/CO mixture at multiple locations along the length of a fixed bed reactor, butadiene in the feed is hydrogenated to butenes while at the same time hydrogenation of butenes to butanes is minimized. It is noted that the use of one or more streams containing H2 and CO also can be used in the embodiment shown in of FIG. 1. The system shown in FIG. 2 is designated as 110. A C4 feed stream, which is designated as 112, is combined with a recycle stream 118 to form stream 120, which is fed to a fixed bed hydroisomerization reactor 122. Hydrogen in stream 116 is fed directly to the hydroisomerization reactor 122 or is combined with streams 112 and 118 to form stream 120. Carbon monoxide optionally is included with the hydrogen in stream 116. Hydrogen and/or carbon monoxide optionally also can be injected into the reactor 122 at a second location approximately midway along the length of the reactor 122 in stream 121. In the hydroisomerization reactor 122, 1-butene is hydroisomerized into 2-butene, forming reactor effluent stream 124. Hydrogen and other non-condensibles are vented from the reactor effluent stream 124 in stream 125.

The remaining reactor effluent in stream 126 is fed to a first fractionating tower 130. In the first fractionating tower 130, C4 compounds are removed from the top in stream 132 and C5+ compounds are removed as bottoms in stream 134. A hydrogenation catalyst bed 131, also known as a "guard bed", hydrogenates remaining butadienes to form butenes.

Stream 132 is subsequently fed to a deisobutylenizer tower 136. The top stream 138 from the deisobutylenizer tower 136 contains isobutylene and isobutane, and small quantities of 1-butene and 2-butene. The bottoms stream 140 contains most of the 2-butene. At the upper end 137 of the deisobutylenizer tower 136, there is an elevation at which the concentrations of 1-butene is at a maximum if no side draw is used. An upper side draw 139 is positioned at this elevation. The side draw 139 forms the liquid recycle stream 118 which is combined with feed stream 112 as is indicated above. The location of the side draw 139 preferably is selected in the same manner as in the embodiment of FIG. 1, i.e. the elevation at which the ratio of 1-butene to 2-butene is at a maximum if no side draw is taken.

Figure 3:
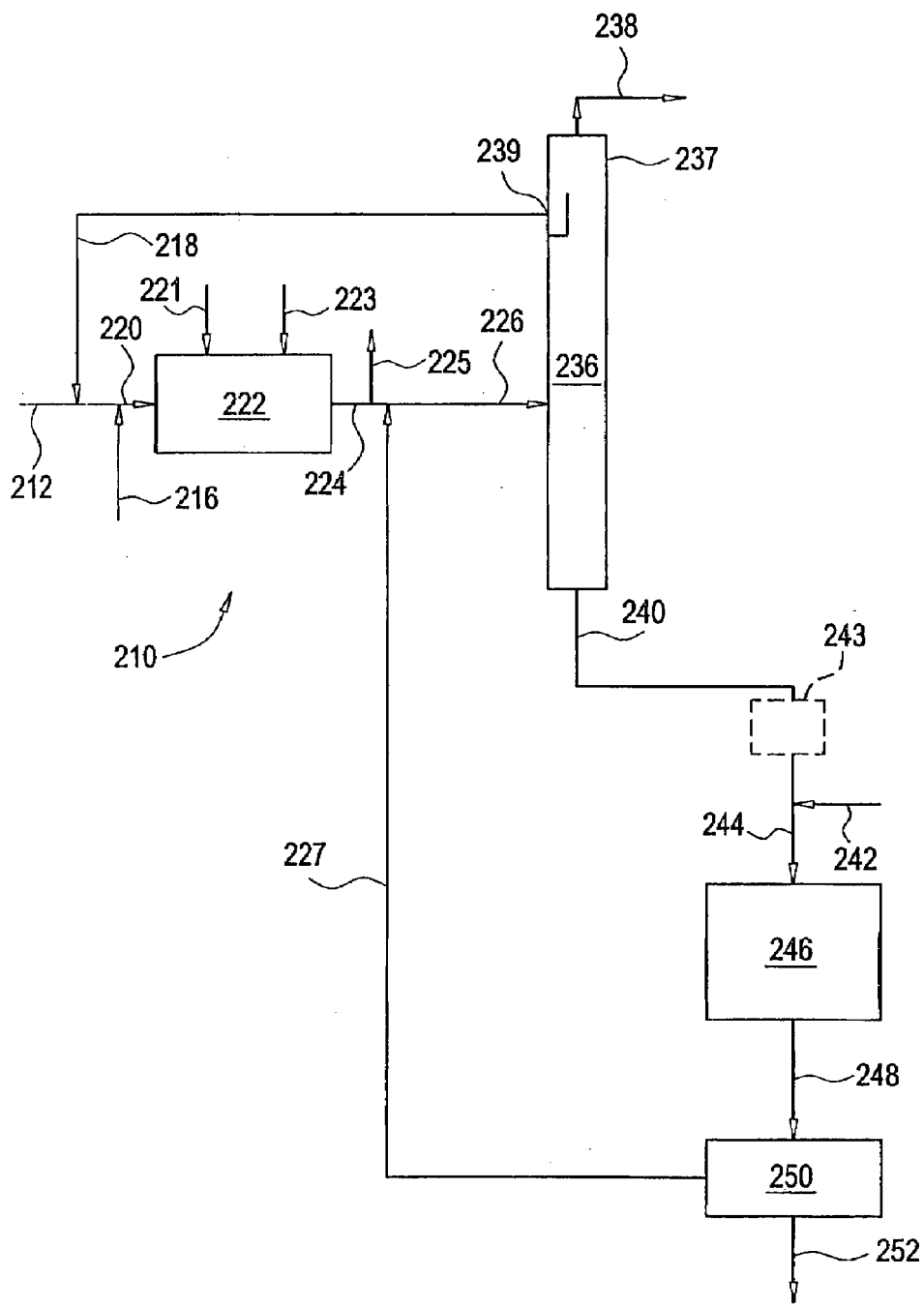
FIG. 3 is a schematic drawing of an embodiment in which a 2-butene stream is produced and used as the feed stream in a metathesis reaction.

FIG. 3 depicts a system 210 for producing propylene from a C4 stream 212. The C4 stream 212 is combined with a recycle stream 218 to form stream 220, which is fed to a fixed bed hydroisomerization reactor 222. Hydrogen in stream 216 is combined with streams 212 and 218 to form stream 220 or can be fed directly to the reactor 222. Carbon monoxide optionally is included with the hydrogen in stream 216. Hydrogen and optionally also carbon monoxide can be injected into the reactor 222 at a second location approximately one third of the way along the length of the reactor 222 in stream 221 and at a third location about two thirds of the way along the length of the reactor 222 in stream 223. If multiple points of injection are used, the volume of the hydrogen and optional carbon monoxide introduced in stream 216 is reduced in order that the overall volume of hydrogen and CO is no more than is necessary to achieve the desired result. The advantage of splitting the hydrogen into three different feed points is to reduce the production of butanes in the reactor 222. The advantage of including carbon monoxide in streams 216, 221 and/or 223 is to inhibit hydrogenation reactions while allowing hydroisomerization reactions to proceed.

When a single injection of a mixed H2/CO stream is used, as is depicted in FIG. 1, the CO and H2 preferably are injected at a single point upstream from the hydroisomerization reactor. In this case, the CO to H2 ratio is between 0.1% and 3% on a molar basis, more preferably 0.1-0.5%, and is typically 0.2-0.4% on a molar basis. When multiple injections are used, as are depicted in FIGS. 2 and 3, hydrogen preferably is apportioned at each feed point in a manner such that the total volume of the catalyst in the hydroisomerization reactor is in an active state. The ratio of CO to H2 at each point of injection preferably, but not necessarily, is the same as at the other points of injection. It is also feasible to have one of the streams contain only hydrogen.

In the hydroisomerization reactor 222, 1-butene is hydroisomerized into 2-butene. The reactor effluent stream 224 is vented to remove hydrogen and other non-condensibles in stream 225 and is then combined with a metathesis recycle stream 227 to form stream 226, which is fed to a deisobutylenizer tower 236. Above the feed point in deisobutylenizer tower 236, at the upper end 237 of the deisobutylenizer tower, there is an elevation at which the concentrations of 1-butene is at a maximum if no side draw is included. An upper side draw 239 is positioned at this location, forming recycle stream 218. Recycle stream 218 is combined with feed stream 212 and enters the hydroisomerization reactor 222 as is indicated above. The top stream 238 from the deisobutylenizer tower 236 contains isobutylene and isobutane, and small quantities of 1-butene and 2-butene. The bottoms stream 240 contains most of the 2-butene. Preferably, the butadiene content of stream 240 is less than 50 parts per million based on weight, and more preferably less than 10 parts per million based on weight, since butadiene is a poison for metathesis catalysts. Stream 240 optionally is purified in one or more guard beds 243. An ethylene feed stream 242 is combined with the bottoms stream 240 to form a metathesis reactor feed stream 244. This stream enters the metathesis reactor 246, in which the 2-butene and ethylene react to form a metathesis product stream 248.

The metathesis product stream 248 contains propylene, butenes and C5+ hydrocarbons. The propylene is separated from the heavier hydrocarbons in separator 250 and is removed as the product in stream 252. The C4, C5 and heavier hydrocarbons are recycled in metathesis recycle stream 227 and are combined with stream 224 to form stream 226.

Figure 4:
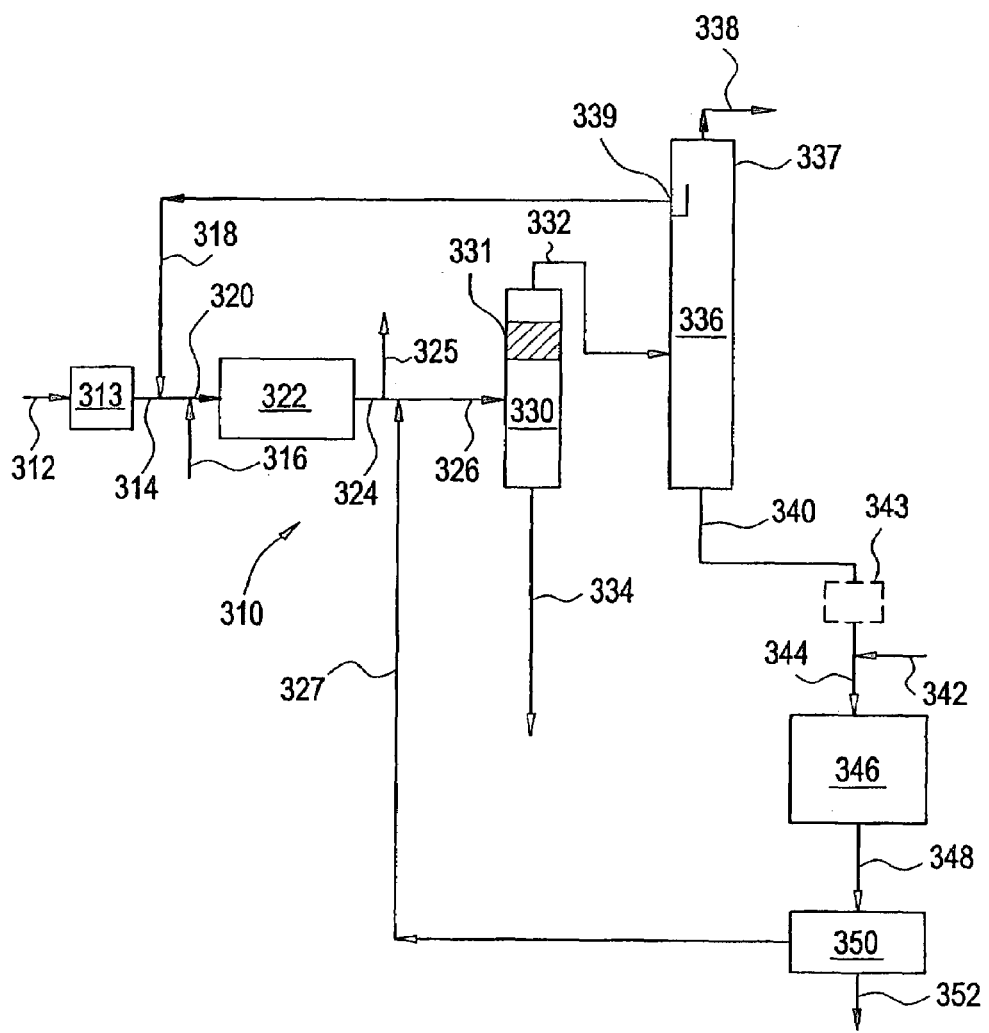
FIG. 4 is a schematic drawing of another embodiment in which a 2-butene stream is produced and used as the feed stream in a metathesis reaction.

FIG. 4 depicts a system 310 for producing propylene from a C4 stream. A C4 feed stream 312 is passed though a selective hydrogenation unit 313 which hydrogenates butadiene, producing a low-butadiene C4 feed stream 314. A hydrogen stream 316 and a recycle stream 318 are combined with stream 314 to form stream 320. Stream 320 is fed to a fixed bed hydroisomerization reactor 322 in which 1-butene is hydroisomerized into 2-butene. The split feed of hydrogen to the hydroisomerization reactor and the inclusion of carbon monoxide with the hydrogen can be used in this embodiment, as well as any of the embodiments of FIGS. 1-4.

The reactor effluent stream 324 is vented to remove hydrogen and other non-condensibles in stream 325 and the remainder is combined with a metathesis recycle stream 327 to form stream 326, which is fed to a fractionating tower 330. In fractionating tower 330, C4 compounds are removed from the top in stream 332 and C5+ compounds are removed as bottoms in stream 334. A hydrogenation catalyst bed 331, also known as a "guard bed", hydrogenates remaining butadienes to form butenes.

Stream 332 is subsequently fed to a deisobutylenizer tower 336. Above the feed point in deisobutylenizer tower 336, at the upper end 337 of the deisobutylenizer tower 336, proximate or at the location at which the concentrations of 1-butene and butadiene are at a maximum, an upper side draw 339 is positioned, the side draw 339 forming recycle stream 318. Recycle stream 318 is combined with feed stream 312 and enters the hydroisomerization reactor 322. The top stream 338 from the deisobutylenizer tower 336 contains isobutylene and isobutane, and small quantities of 1-butene and 2-butene. The bottoms stream 340 contains the 2-butene. Stream 340 optionally is purified in one or more guard beds 343. An ethylene feed stream 342 is combined with the bottoms stream 340 to form a metathesis reactor feed stream 344. This stream enters the metathesis reactor 346, in which the 2-butene and ethylene react to form a metathesis product stream 348.

The metathesis product stream 348 contains propylene, butenes and C5+ hydrocarbons. The propylene is separated from the heavier hydrocarbons in separator 350 and is removed as the product in stream 352. The C4, C5 and heavier hydrocarbons are recycled in stream 327 and are combined with the debutanizer feed from stream 324 (usually after venting) in stream 326.

The removal of a side draw and recycling of the side draw back to the hydroisomerization reactor provides several processing advantages. First, by removing 1-butene from the top of the deisobutylenizer tower and recycling it to the hydroisomerization reactor, a lower rate of conversion from 1-butene to 2-butene can be employed in the hydroisomerization reactor, thereby resulting in a lower rate of conversion of butenes to butanes. As a result, more butenes exit from the deisobutylenizer tower, resulting in a higher rate of propylene production for a given quantity of C4 feed when the system is followed by a metathesis reaction. Second, by removing butadiene in a recycle stream, a lower concentration of butadiene will be found in the bottoms stream. This reduction in butadiene in turn reduces the fouling of the metathesis catalyst in the metathesis reactor. Third, the recycle stream causes a greater proportion of the 1-butene to be recycled rather than being removed at the top of the fractionation tower with the isobutylene and isobutane. This results in a greater quantity of 1-butene being converted to 2-butene in the overall process.

The invention is particularly useful for processing stream cracker C4 streams and refinery C4 streams. Typically, steam cracker C4 streams contain appreciable quantities of butadiene and therefore require inclusion of a selective hydrogenation unit to convert butadiene to butenes. Refinery C4 streams have a low butadiene content that can be processed within the hydroisomerization unit, and thus inclusion of a selective hydrogenation unit is not required. The inclusion of a fractionator upstream from the deisobutylenizer tower provides for the removal of heavy materials that enter the system along with the C4s. Refinery C4 streams often contain heavier sulfur compounds including dimethyl disulfide (DMDS) and diethyl disulfide (DEDS), both of which can be removed by a first fractionating tower, as is shown in FIGS. 2 and 4.

EXAMPLES

The examples show various processing options for a single C4 feed stream having the composition shown below on Table 1. While any type of C4 stream can be used in the invention, such streams typically are generated from a steam cracker C4 stream, a C4 stream from an FCC unit, or a mixture of the two.

TABLE 1

C4 LIQUID Feed

| Feed Rate | kg/hr | 39317 |
|---|---|---|
| Molecular Weight | | 56.71 |

| | wt % |
|---|---|
| Hydrogen | 0.00 |
| Methane | 0.03 |
| Propylene | 0.33 |
| Propane | 0.85 |
| 13 Butadiene | 0.13 |
| 1-Butene | 11.63 |
| Cis-2-Butene | 9.66 |
| Trans-2-butene | 15.97 |
| Isobutylene | 18.73 |
| Isobutane | 28.57 |
| n-Butane | 14.02 |
| n-Pentane | 0.08 |
| Total | 100.00 |

The methane is soluble methane from an upstream selective hydrogenation unit where the butadiene has been reduced from approximately 45,000 ppmw in the feed to 1300 ppmw in the effluent. The hydrogen for that reaction contains some quantities of methane. As a result of the selective hydrogenation step, the total 2-butenes are 26.63 wt % and the 1-butene is 11.63 wt %. This results in a 2-butene to 1-butene ratio of 2.29. This is far from the hydroisomerization equilibrium ratio at the nominal hydroisomerization reactor temperature of 60 deg. C. At 60 deg. C., the equilibrium ratio of 2-butene to 1-butene is 21.6. The hydrogen used in the examples consists of a mixture of 95 wt. % hydrogen and 5 wt. % methane, with a molecular weight of 2.11.

In the fixed bed hydroisomerization reactor, the 1-butene is reacted to form 2-butene and the remaining butadiene is hydrogenated to 1-butene. There is also reaction of the 1-butene in the feed (and/or formed from butadiene) to n-butane. The selectivity is defined as that portion of the 1-butene converted that is converted to n-butane. In this particular example, the equilibrium mixture of 1-butene and 2-butene would result in the conversion of 84.9% of the 1-butene. Note that complete conversion can not be obtained in a single step due to the limitation of equilibrium.

Figure 5:
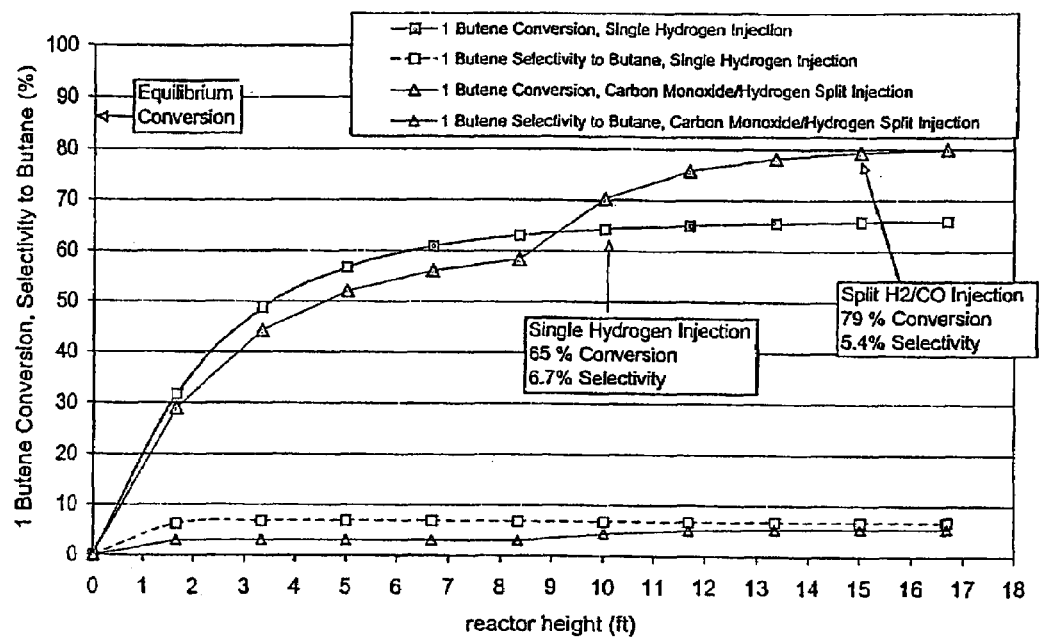
FIG. 5 is a graph showing conversion and selectivity profiles for the hydroisomerization of 1-butene to 2-butene.

FIG. 5 shows the conversion/selectivity for reaction of the C4 stream over a hydroisomerization reactor containing a supported Pd catalyst. FIG. 5 shows the performance when using a single pure hydrogen feed and the improvement which can result from the use of small quantities of CO with hydrogen injected at multiple feed points in the hydroisomerization reactor. When a single hydrogen injection point is used in a 10 ft. L×4.5 ft. ID hydroisomerization reactor, the conversion to 1-butene is 65% with a selectivity to n-butene of 6.7%. Selectivity to butane is defined as the total butane produced divided by the 1-butene converted. As described above, under normal conditions, butane is formed simultaneously as the 1-butene is hydroisomerized to 2-butene. When two hydrogen/CO feeds are used, the rate of reaction is suppressed slightly and the selectivity to butane is reduced. A 15 ft. L×4.5 ft. ID hydroisomerization reactor containing more catalyst is used and the conversion improves to 79% with 5.4% selectivity to n-butane. For the feedstock shown and for the temperature of the reactor, the equilibrium conversion (without hydrogenation) is 84.9%.

Figure 6:
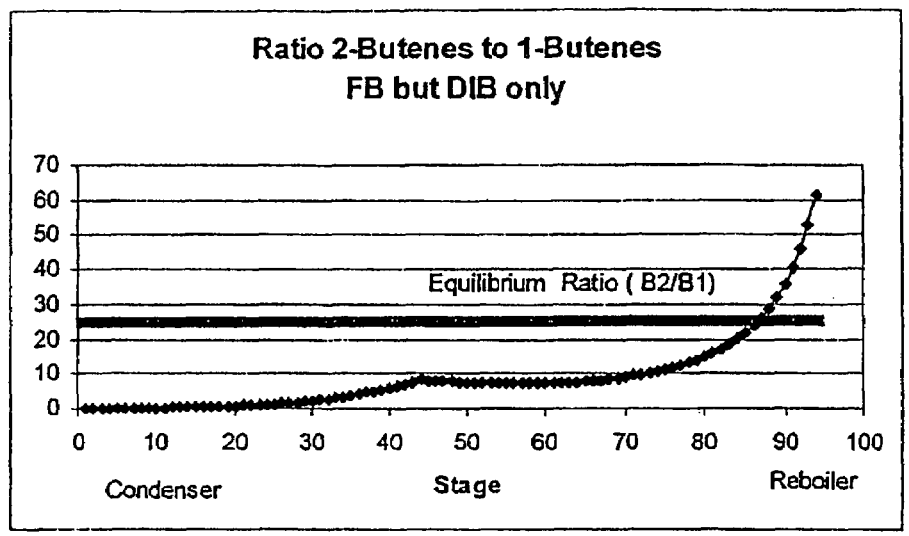
FIG. 6 is a graph showing the ratio of 1-butenes to 2-butenes in a deisobutylenizer tower which is downstream from a fixed bed reactor.

It is important to define the proper location for the sidedraw. The location preferably is the point of maximum driving force for the hydroisomerization reaction. This location is defined by considering the composition profiles of the tower using a fixed bed only (no side draw). The composition profile over the tower for Example 2 with a side draw of 0 is shown in FIG. 6. FIG. 6 shows the ratio of 2-butene to 1-butene. As can be seen, for most of the tower, the ratio is below equilibrium indicating potential favorable reaction of 1-butene to 2-butene.

Figure 7:
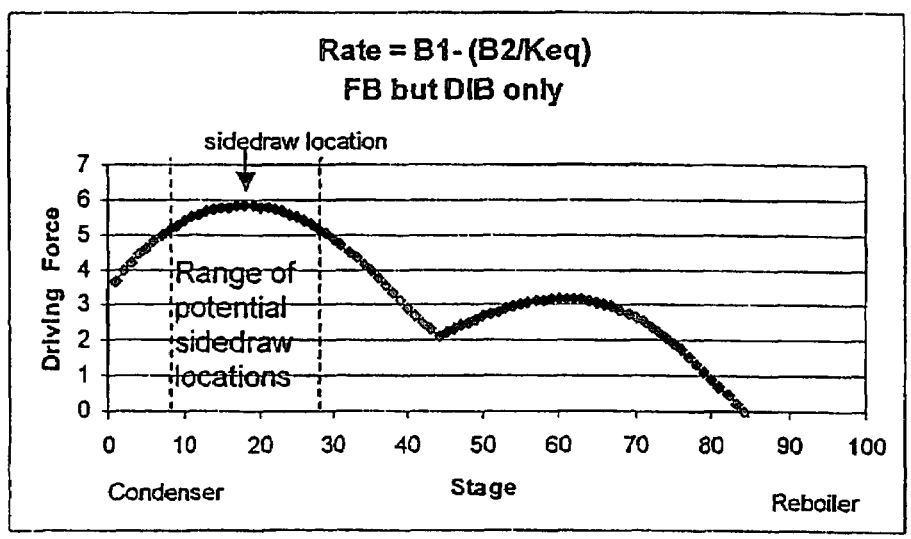
FIG. 7 is a graph showing the driving force at various stages in a deisobutylenizer tower which does not have a side draw for removal of 2-butenes near the top of the column.
Figure 8:
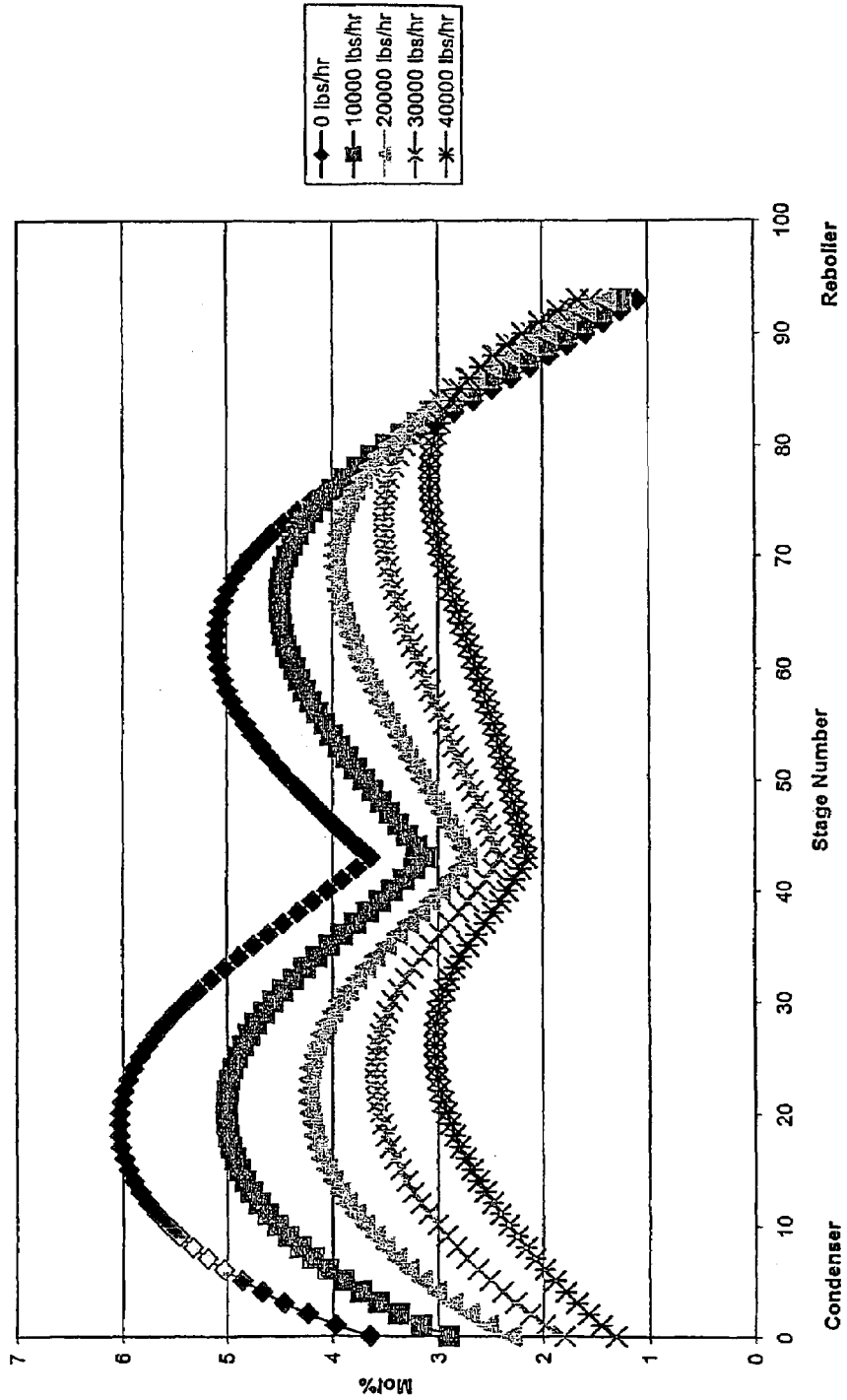
FIG. 8 is a graph showing the 1-butene content at various stages of a deisobutylenizer tower when there is no side draw from the top of the column and when side draws of various flow rates are employed.

FIG. 7 shows the "driving force" as defined above. As can be seen, the potential locations for removal of a side draw are between stages 9 and 29 with the optimal location at stage 18. This location will vary depending upon the specifics of the feedstock and fractionation operating conditions. It is however desired that the location be at or near the point of optimal driving force with preferred locations having driving forces at least 85% of the maximum, and usually at least 90% of the maximum, as defined by the composition profile without side draw. FIG. 8 shows the impact of the side draw rate on the 1-butene composition in the fractionation column. A larger side draw results in a lower 1-butene concentration at the top of the column.

Example 1 (Comparative)

Conventional CD-DeIB Tower

A sophisticated computerized simulation was run in which feed streams having the composition shown above were sent to three different conventional CD-DeIB towers. A total of 10109 lb/hr of 1-butene is in the feed. In addition there is 22235 lb/hr of 2-butene and 116 lb/hr of butadiene. The first tower, Tower 1A, consisted of 94 equilibrium stages and a reflux ratio of 4.5 (reflux to feed). This tower contained 23581 lb of catalyst in 2042 ft$^3$ of catalytic distillation structures. This represents an approximate space velocity of 2.3 weight catalyst per weight 1-butene fed to the tower. The balance of the tower was filled with high efficiency fractionation packing. Hydrogen was added below the catalyst beds and below the feed to supply the required hydrogenation of butadiene and 1-butene hydroisomerization. The second tower, Tower 1B, consisted of 129 equilibrium stages and had a reflux ratio of 4.5 (reflux to feed). The additional 35 stages helped to achieve better separation. This tower also contained 23581 lb of catalyst in 2042 ft$^3$ of structures. The balance of the tower was filled with high efficiency fractionation packing. Hydrogen was added to supply the required hydrogenation of butadiene and 1-butene hydroisomerization. The third tower, designated as Tower 1C, consisted of 94 equilibrium stages and operated at a reflux ratio of 6.20 (reflux to feed). The higher reflux improved fractionation but required more utilities (reboiling and condensing duty). This tower also contained 23581 lb of catalyst in 2042 ft$^3$ of structures. The balance of the tower was filled with high efficiency fractionation packing. Hydrogen was added to supply the required hydrogenation of butadiene and 1-butene hydroisomerization.

In a CD-DeIB tower of the prior art, fractionation and hydroisomerization proceed in parallel. Over a multiplicity of stages, the 1-butene reacts to form 2-butene while simultaneously the 2-butene moves downward by fractionation and the 1-butene moves upward by fractionation. Thus, as the mixture moves upward through the tower, the reaction mixture is continually moving away from equilibrium by fractionation and toward equilibrium via reaction. In order to achieve high conversion, a multiplicity of reaction stages are required to match the multiplicity of fractionation stages. This results in a large amount of catalyst. This sequence occurs in all three towers.

In all of the three towers, the feedstock is as shown in Table 1. There is a considerable amount of 1-butene and butadiene in the feed. It is the objective of the design to produce a bottoms stream containing a high fraction of 2-butene and minimal amount of butadiene. As discussed above, the 1-butene tends to rise in the tower and the butadiene tends to move lower. This impacts the performance of the tower in that fractionation conditions must be varied to achieve a mixture with low butadiene.

As is shown on Table 2, in Tower 1A there was insufficient fractionation to achieve a high recovery of n-butenes in the bottoms as desired for a metathesis process. Since the feed to the tower is unreacted, the overhead product rate had to be increased to move the butadiene up the tower and thus over the hydrogenation/hydroisomerization catalyst. This was required to reduce the butadiene in the effluent to 10 ppm. With the higher overhead product flow, significant 2-butene was lost overhead. The recovery was 76.1% of the feed as n-butenes in the bottoms when meeting a low butadiene level in the bottoms product. It is also important to note that when the butadiene must be pushed overhead a greater amount of hydrogenation occurs resulting in a higher selectivity to butane. This is undesirable.

In Tower 1B, an increased number of fractionation stages (129 versus 94) were used to improve recovery. The recovery increased to 91%. This option required more capital cost in the fractionation tower.

Tower 1C used reflux to improve fractionation performance. In this case, a higher reflux ratio (6.2 versus 4.5) was used. This improved the recovery to 93.8%. However, this option required more capital cost due to the higher traffic in the tower needed a larger tower diameter. Further, the energy requirement was greater due to the higher reboiler and condenser duties.

TABLE 2

| | | Example Number | | |
|---|---|---|---|---|
| | | Comp. 1A | Comp. 1B | Comp. 1C |
| Number of Stages | | 94 | 129 | 94 |
| Reflux Rate | lb/hr | 400000 | 400000 | 550000 |
| Total Feed Rate | lb/hr | 88689 | 88689 | 88689 |
| % Feed nButenes in Bottoms | wt % | 76.10 | 91.25 | 93.80 |
| i-butylene in Bottoms, | wt % | 0.06 | 0.02 | 0.05 |
| 13 BD in Bottoms | ppmw | 10 | 10 | 10 |
| 1-Butene in Distillate | lb/hr | 1535 | 1135 | 984 |
| 2-Butenes in Distillate | lb/hr | 5104 | 1588 | 899 |
| 1-Butene in Bottoms | lb/hr | 24 | 15 | 23 |
| 2-Butenes in Bottoms | lb/hr | 24596 | 29498 | 30318 |
| Selectivity to N butane (Saturation) Conversions and Selectivity | % | 13.5 | 2.4 | 2.5 |
| 1-Butene in | lb/hr | 10109 | 10109 | 10109 |
| 1-Butene out | lb/hr | 1586 | 1154 | 1011 |
| 1-Butene Conversion | wt % | 84 | 89 | 90 |

TABLE 2-continued

| | | Example Number | | |
|---|---|---|---|---|
| | | Comp. 1A | Comp. 1B | Comp. 1C |
| n-Butane in | lb/hr | 12174 | 12174 | 12174 |
| n-Butane out Utilities | lb/hr | 13327 | 12389 | 12400 |
| Reboiler | MMkcal/hr | 17.54 | 17.02 | 22.30 |
| Condenser Catalyst | MMkcal/hr | 17.11 | 16.69 | 21.70 |
| Catalyst Amount (Tower) | lb | 23581 | 23581 | 23581 |
| Catalyst Volume (Structure) | ft3 | 2042 | 2042 | 2042 |

Example 2

Side Draw from Deisobutylenizer Tower

A sophisticated computerized simulation was run in which a feed stream having the same composition of the feed streams used in Comparative Example 1 was sent to a 10 ft L×4.5 ft ID fixed bed hydroisomerization unit. As described above, this reactor used a single hydrogen feed and had a conversion of 1-butene of 66%. Following the fixed bed, the effluent flowed to a fractionation tower to separate the isobutylene and isobutane from the 2-butene and n-butane. The tower following the fixed bed consisted of 94 theoretical stages with a reflux ratio of 4.5. The simulated reactor was a fixed bed with 6.7% 1-butene selectivity to butane. The reboiler and condenser duties were equivalent to those of CD-DeIB Tower 1A in Comparative Example 1 since they are set by the reflux ratio. The process resulted in a 66% conversion of 1-butene (Comparative Example 2). The results are shown on Table 3. This represents the performance of the prior art fixed bed plus fractionation system. A total of 90.3% of the normal butenes (1- and 2-butenes) are recovered in the bottoms product.

The above process was repeated with the exception that a side draw was removed from the fractionation tower at stage 18 in an amount of 10,000 (Example 2A) or 20,000 lb/hr (Examples 2B-2C). The results are shown on Table 3. A side draw of 10,000 lb/hr resulted in an increase in the amount of n-butene recovery (including 2-butene) in the bottoms from 90.33% to 93.87%. This is a result of the higher 1-butene conversion made possible by the recycle of the side draw. A side draw of 20,000 lb/hr resulted in a n-butene recovery in the bottoms of 96.73% (Example 2B). However, the isobutylene content in the bottoms was also relatively high at 17.87%. For the two cases having a 20,000 lb/hr side draw, the difference is the amount of distillate product that is taken. When the tower was adjusted to have a 2.73% isobutylene content in the bottoms, the % of the n-butene feed in the bottoms was 92.55% (Example 2C). The distillate product (overhead) rate controls the amount of isobutylene and butadiene that is in the bottoms product. In order to achieve a lower amount of isobutylene in the bottoms product, there are several options. A higher distillate product flow can be taken, more stages can be employed, or more reflux can be used. All are commercially useful options. For this example, the fractionation tower was assumed to remain the same at 94 theoretical stages and a fixed reflux ratio of 4.5. It is important to note that in all cases, the butadiene is lower than that obtained under similar conditions for the CD-DeIB. This is the result of the butadiene conversion in the hydroisomerization reactor upstream of the fractionating tower.

For all cases, the quantity of catalyst required for all of the fixed bed cases is considerably reduced from that required for the CD-DeIB. As described, that system uses a high amount of catalyst by the nature of its reaction sequence within the tower.

TABLE 3

|  |  | Example Number | | | |
|---|---|---|---|---|---|
|  |  | Comp. 2 | 2A | 2B | 2C |
| Sidedraw rate | kg/hr | 0 | 10000 | 20000 | 20000 |
| Reflux Rate | lb/hr | 400000 | 400000 | 400000 | 400000 |
| Total Feed Rate | lbs/hr | 88689 | 88689 | 88689 | 88689 |
| % Feed nButenes in Bottoms | wt % | 90.33 | 93.87 | 96.73 | 92.55 |
| i-butylene in Bottoms, | wt % | 3.55 | 8.9 | 17.87 | 2.73 |
| 13 BD in Bottoms | ppmw | 10 | 10 | 10 | 4 |
| 1-Butene in Distillate | lb/hr | 2706 | 1558 | 667 | 1844 |
| 2-Butenes in Distillate | lb/hr | 117 | 58 | 15 | 161 |
| 1-Butene in Bottoms | lb/hr | 770 | 1122 | 1584 | 424 |
| 2-Butenes in Bottoms | lb/hr | 28447 | 29241 | 29701 | 29511 |
| 13 BD Conversion | wt % | 99 | 99 | 99 | 99 |
| Conversion & Selectivity |  |  |  |  |  |
| 1-Butene in | lb/hr | 10109 | 10109 | 10109 | 10109 |
| 1-Butene out | lb/hr | 3476 | 2681 | 2252 | 2269 |
| 1-Butene Conversion | wt % | 65 | 73 | 78 | 78 |
| n-Butane in | lb/hr | 12174 | 12174 | 12174 | 12174 |
| n-Butane out | lb/hr | 12613 | 12665 | 12709 | 12695 |
| Selectivity to n-Butane (Saturation) Catalyst | wt % | 6.6 | 6.6 | 6.8 | 6.6 |
| Catalyst Amount (Fixed Bed) | lb | 8160.0 | 9588.0 | 9996.0 | 9996.0 |
| Catalyst Volume (Fixed Bed) | ft3 | 160.0 | 188.0 | 196.0 | 196.0 |

Example 3

Side Draw from Deisobutylenizer Tower Combined with Split of Feed of Hydrogen and CO in Hydroisomerization Reactor The procedure of Comparative Example 2 was repeated with the exceptions that a combined feed of hydrogen and CO was added at two different locations along the length of the hydroisomerization reactor, and the simulated reactor was a fixed bed with 5.4% 1-butene saturation.

This case shows improved performance over Comparative Example 2. The recovery is higher at equivalent fractionation conditions. The catalyst volumes are higher reflecting the slightly reduced activity but higher selectivity due to the use of CO. The use of two $H_2$/CO streams increases the recovery to 93.8% (Example 3) from 90.3 (Example 2) as a result of the lower losses of butenes to n-butane (improved selectivity). While this Example requires more catalyst than Comparative Example 2, both Comparative Example 2 and Example 3 require substantially lower catalyst quantities than the CD-DeIB cases of Comparative Example 1.

The procedure of Example 3 was repeated with the exception that a side draw was added at stage 18 in an amount of 10,000 lb/hr. This side draw was mixed with the C4 feed stream and re-injected into the hydroisomerization reactor. Use of the side draw increased the % recovery of n-butenes in the bottoms from 93.82% (Example 3) to 96.21% (Example 3A).

The procedure of Example 3A was repeated with the exception that the side draw at stage 18 was increased to an amount of 20,000 lb/hr. This side draw was mixed with C4 feed stream and re-injected into the hydroisomerization reactor. Use of the increased side draw increased the % recovery of n-butenes in the bottoms from 96.21% (Example 3A) to 97.72% (Example 3B). Note that under identical tower operating specifications (Examples 3, 3A, and 3B), Example 3B resulted in an increase in isobutylene in the bottoms increasing to over 17%. In some cases this is undesirable for downstream processing.

The procedure of Example 3B was repeated with the exceptions that a side draw was added at stage 18 in an amount of 20,000 lb/hr and the tower was adjusted to have a 2.85 wt % isobutylene content in the bottoms. The side draw was mixed with the C4 feed stream and re-injected into the hydroisomerization reactor. At approximately the same isobutylene in the bottoms product, the use of the side draw increased the % recovery of n-butenes in the bottoms from 93.82% (Example 3A) to 95.08% (Example 3C). Note however, by increasing the overhead product flow to recover more isobutylene overhead, the net recovery of n-butenes in the bottoms product dropped from 97.72% to 95.08%. The results are shown on Table 4.

TABLE 4

|  |  | Example Number | | | |
|---|---|---|---|---|---|
|  |  | 3 | 3A | 3B | 3C |
| Sidedraw rate | kg/hr | 0 | 10000 | 20000 | 20000 |
| Reflux Rate | lb/hr | 400000 | 400000 | 400000 | 400000 |
| Total Feed Rate | lb/hr | 88689 | 88689 | 88689 | 88689 |
| % Feed nButenes in Bottoms | wt % | 93.82 | 96.21 | 97.72 | 95.08 |
| i-butylene in Bottoms, | wt % | 3.73 | 9.37 | 18.4 | 2.85 |
| 13 BD in Bottoms | ppmw | 10 | 10 | 10 | 4 |
| 1-Butene in Distillate | lb/hr | 1591 | 875 | 359 | 1087 |
| 2-Butenes in Distillate | lb/hr | 107 | 52 | 14 | 150 |
| 1-Butene in Bottoms | lb/hr | 487 | 687 | 944 | 265 |
| 2-Butenes in Bottoms | lb/hr | 29861 | 30432 | 30664 | 30490 |
| Conversion & Selectivity |  |  |  |  |  |
| 1-Butene in | lb/hr | 10109 | 10109 | 10109 | 10109 |
| 1-Butene out | lb/hr | 2077 | 1562 | 1303 | 1351 |
| 1-Butene Conversion | wt % | 79 | 85 | 87 | 87 |
| n-Butane in | lb/hr | 12174 | 12174 | 12174 | 12174 |
| n-Butane out | lb/hr | 12607 | 12645 | 12647 | 12661 |
| Selectivity to n-Butane (Saturation) Catalyst | wt % | 5.4 | 5.4 | 5.4 | 5.4 |

TABLE 4-continued

| | | Example Number | | | |
|---|---|---|---|---|---|
| | | 3 | 3A | 3B | 3C |
| Catalyst Amount (Fixed Bed) | lb | 12240.0 | 14382.0 | 14994.0 | 14994.0 |
| Catalyst Volume (Fixed Bed) | ft3 | 240.0 | 282.0 | 294.0 | 294.0 |

As can be seen, the use of a side draw resulted in higher n-butene recovery than the cases with a fixed bed only followed by a conventional tower with no sidedraw (Comparative Example 2) or a CD-DeIB alone (Example 1). In all cases, the catalyst costs for the fixed bed options are lower than for the CD-DeIB.

In summary, the comparisons at the same fractionation conditions (94 theoretical trays and reflux ratio=4.5) are:

TABLE 5

| | Case | | | |
|---|---|---|---|---|
| | Comp. Ex. 2 fixed bed only | Ex. 2A fixed bed w/side draw | Comp. Ex. 1A CD-DelB | Ex. 3C Fixed bed with $H_2$/CO and side draw |
| N-Butene Recovery | 90.33 | 93.9 | 76.1 | 95.1 |
| | Some improvement possible with increased stages and/or reflux | Some improvement possible with increased stages and/or reflux | Can improve to 93% with increased stages (35 more) or reflux (38% more) | Can increase to 98% if let isobutylene increase in bottoms or use increased stages and/or reflux |

As will be apparent to persons skilled in the art, various of the above-disclosed and other features and functions, or alternatives thereof, may be desirably combined into many other different systems or applications. Furthermore, various presently unforeseen or unanticipated alternatives, modifications, variations or improvements therein may be subsequently made by those skilled in the art which are also intended to be encompassed by the following claims.

What is claimed is:

1. A process for the preferential conversion to 2-butene of a C4 stream containing 1-butene and 2-butene, comprising:
    mixing said C4 stream with a first hydrogen stream to form a feed stream,
    hydroisomerizing said feed stream in the presence of a hydroisomerization catalyst in order to convert at least a portion of said 1-butene to 2-butene, thereby producing a hydroisomerization effluent,
    passing said hydroisomerization effluent through a fractionation column to form a top stream comprising isobutane and isobutylene and a bottoms stream comprising 2-butene,
    withdrawing a recycle stream from said fractionation column at a location above the feed point at which the weight ratio of 1-butene to 2-butene is high, and
    combining said recycle stream with at least one of said C4 stream and said feed stream upstream from said hydroisomerization catalyst.

2. The process of claim 1, wherein said C4 stream further comprises butadiene, further comprising hydrogenating said C4 stream before or during mixing of said C4 stream with said first hydrogen stream to reduce the butadiene content of said C4 stream to no more than about 1 wt %.

3. The process of claim 2, wherein said recycle stream is mixed with said C4 stream after said C4 stream has been mixed with said first hydrogen stream.

4. The process of claim 1, wherein said recycle stream is withdrawn at the elevation in said column at which the 1-butene concentration would be at a maximum if no recycle stream were withdrawn.

5. The process of claim 1, further comprising mixing said bottoms stream with a suitable metathesis reactant to form a metathesis feed stream, and feeding said metathesis feed stream to a metathesis reactor and reacting said 2-butene with said metathesis reactant to form a metathesis product.

6. The process of claim 2, further comprising mixing said bottoms stream with a suitable metathesis reactant to form a metathesis feed stream, and feeding said metathesis feed stream to a metathesis reactor and reacting said 2-butene with said metathesis reactant to form a metathesis product.

7. The process of claim 5, wherein said metathesis reactant comprises ethylene and said metathesis product comprises propylene.

8. The process of claim 1, wherein said C4 stream includes C5 and/or heavier components, further comprising removing said C5 and/or heavier components from said hydroisomerization effluent before passing said hydroisomerization effluent through said fractionation column.

9. The process of claim 5, further comprising purifying one of said bottoms stream and said metathesis feed stream before feeding said metathesis feed stream to said metathesis reactor.

10. The process of claim 1, further comprising feeding a second hydrogen stream to said hydroisomerization reactor at a location downstream from the feed point of said first hydrogen stream.

11. The process of claim 10, further comprising feeding a third hydrogen stream to said hydroisomerization reactor at a location downstream from the feed point of said second hydrogen stream.

12. The process of claim 1, wherein said first hydrogen stream further comprises carbon monoxide.

13. The process of claim 10, wherein at least one of said first and second hydrogen streams further comprises carbon monoxide.

14. The process of claim 11, wherein at least one of said first, second and third hydrogen streams further comprises carbon monoxide.

15. The process of claim 5, wherein said first hydrogen stream further comprises carbon monoxide.

16. The process of claim 5, further comprising separating said metathesis product from heavier components to form a heavy component stream and combining said heavy component stream with said hydroisomerization effluent.

17. The process of claim 1, wherein the recycle stream is withdrawn at the elevation in said fractionation column at which the driving force for the hydroisomerization of 1-butene to 2-butene would be at least 85% of the maximum driving force within said column if no recycle stream were withdrawn.

18. The process of claim 1, wherein the recycle stream is withdrawn at the elevation in said fractionation column at which the driving force for the hydroisomerization of 1-butene to 2-butene would be at least 90% of the maximum driving force within said column if no recycle stream were withdrawn.

19. The process of claim 1, wherein said hydroisomerization catalyst comprises a group VIII metal on a support.

20. The process of claim 19, wherein said hydroisomerization catalyst includes an additive selected from the group consisting of gold, silver, and alkali metals.

21. A process for the production of propylene from a C4 stream containing butadiene, 1-butene, and 2-butene, comprising:

mixing said C4 stream with a first hydrogen stream to hydrogenate butadiene and form a feed stream having a butadiene content of no more than about 1 wt %, hydroisomerizing said feed stream in the presence of a hydroisomerization catalyst in order to convert at least a portion of said 1-butene to 2-butene, thereby producing a hydroisomerization effluent, passing said hydroisomerization effluent through a fractionation column to form a top stream comprising isobutane and isobutylene and a bottoms stream comprising 2-butene, withdrawing a recycle stream from said fractionation column at a location in said column at which the weight ratio of 1-butene to 2-butene is at a maximum, combining said recycle stream with at least one of said C4 stream and said feed stream upstream from said hydroisomerization catalyst, mixing said bottoms stream with ethylene to form a metathesis feed stream, and feeding said metathesis feed stream to a metathesis reactor and reacting said 2-butene with said ethylene to form propylene.

* * * * *

UNITED STATES PATENT AND TRADEMARK OFFICE
CERTIFICATE OF CORRECTION

| | |
|---|---|
| PATENT NO. | : 7,576,251 B2 |
| APPLICATION NO. | : 11/107649 |
| DATED | : August 18, 2009 |
| INVENTOR(S) | : Gartside et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1120 days.

Signed and Sealed this

Seventh Day of September, 2010

David J. Kappos
*Director of the United States Patent and Trademark Office*